(12) United States Patent
Pusnik et al.

(10) Patent No.: US 7,077,847 B2
(45) Date of Patent: Jul. 18, 2006

(54) TARGETING DEVICE FOR LOCKING NAILS

(75) Inventors: Peter Pusnik, Kiel (DE); Sabine Bigdeli, Felde (DE)

(73) Assignee: Stryker Trauma GmbH (DE)

( * ) Notice: Subject to any disclaimer, the term of this patent is extended or adjusted under 35 U.S.C. 154(b) by 536 days.

(21) Appl. No.: 10/389,542

(22) Filed: Mar. 14, 2003

(65) Prior Publication Data

US 2003/0220651 A1    Nov. 27, 2003

(30) Foreign Application Priority Data

Mar. 15, 2002    (DE)    ............ 202 04 126 U

(51) Int. Cl.
*A61B 17/58*    (2006.01)

(52) U.S. Cl. ..................................... 606/96

(58) Field of Classification Search ............ 606/96–98, 606/86, 80; 408/115 R
See application file for complete search history.

(56) References Cited

U.S. PATENT DOCUMENTS

| | | | |
|---|---|---|---|
| 5,176,681 A | 1/1993 | Lawes et al. | |
| 5,334,192 A | 8/1994 | Behrens | |
| 5,346,496 A | 9/1994 | Pennig | |
| 6,039,739 A | 3/2000 | Simon | |
| 6,126,661 A | 10/2000 | Faccioli et al. | |
| 6,183,477 B1 | 2/2001 | Pepper | |

FOREIGN PATENT DOCUMENTS

DE    298 06 564 U1    9/1999

*Primary Examiner*—Eduardo C. Robert
*Assistant Examiner*—Michael J. Araj
(74) *Attorney, Agent, or Firm*—Lerner, David, Littenberg, Krumholz & Mentlik, LLP

(57) ABSTRACT

A targeting apparatus for locking nails, has a connecting portion which is adapted to be fixedly connected to the end of a locking nail. The targeting apparatus has an arm which is connected to the nail connecting portion via a U or L-shaped portion. The arm has a plurality of bores to receive a drill guide sleeve wherein the bores are disposed at different angles. The targeting arm has supported thereon a rotatable sleeve but substantially is axially displaceable and has a series of cross-bores or apertures which are circumferentially and axially spaced wherein in the predetermined rotational positions of the rotatable sleeve, at least one aperture is aligned with a bore in the targeting arm. A detent is provided which locks the rotatable sleeve on the targeting arm in the selected individual rotational positions.

19 Claims, 4 Drawing Sheets

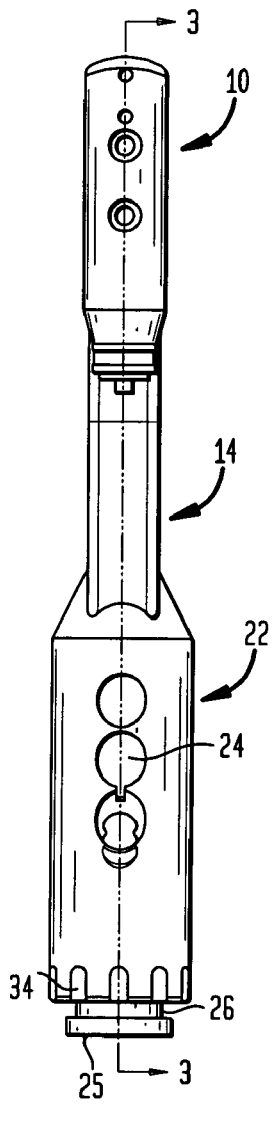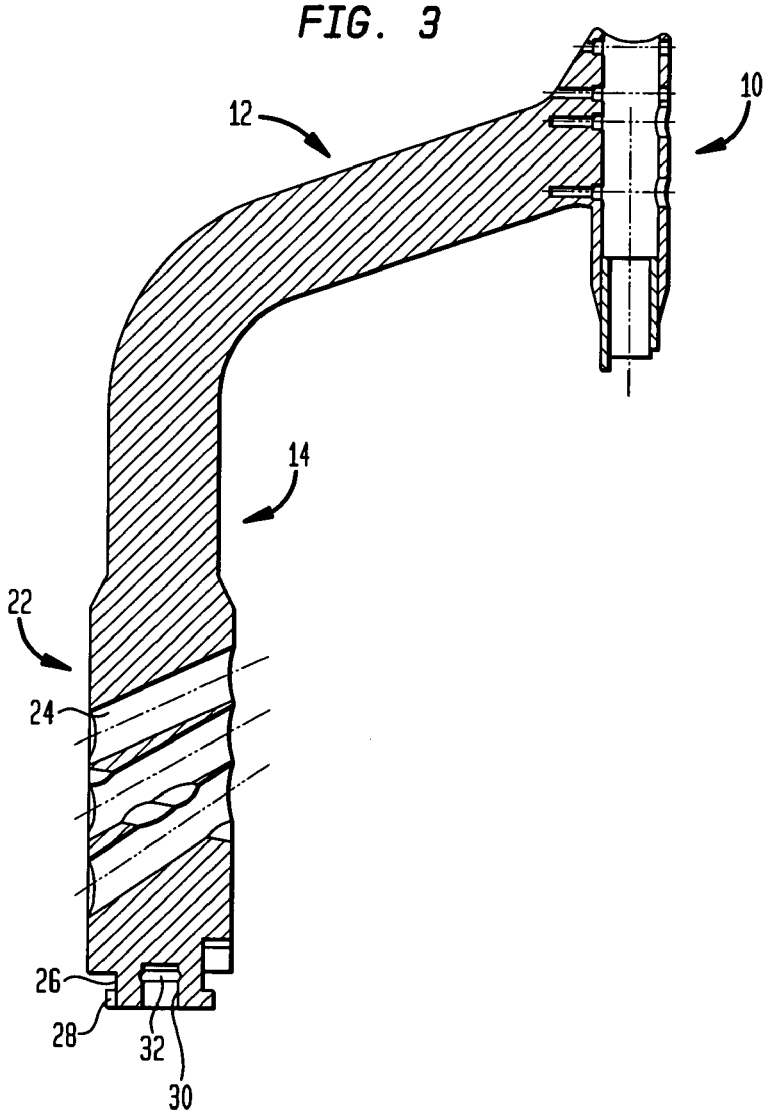

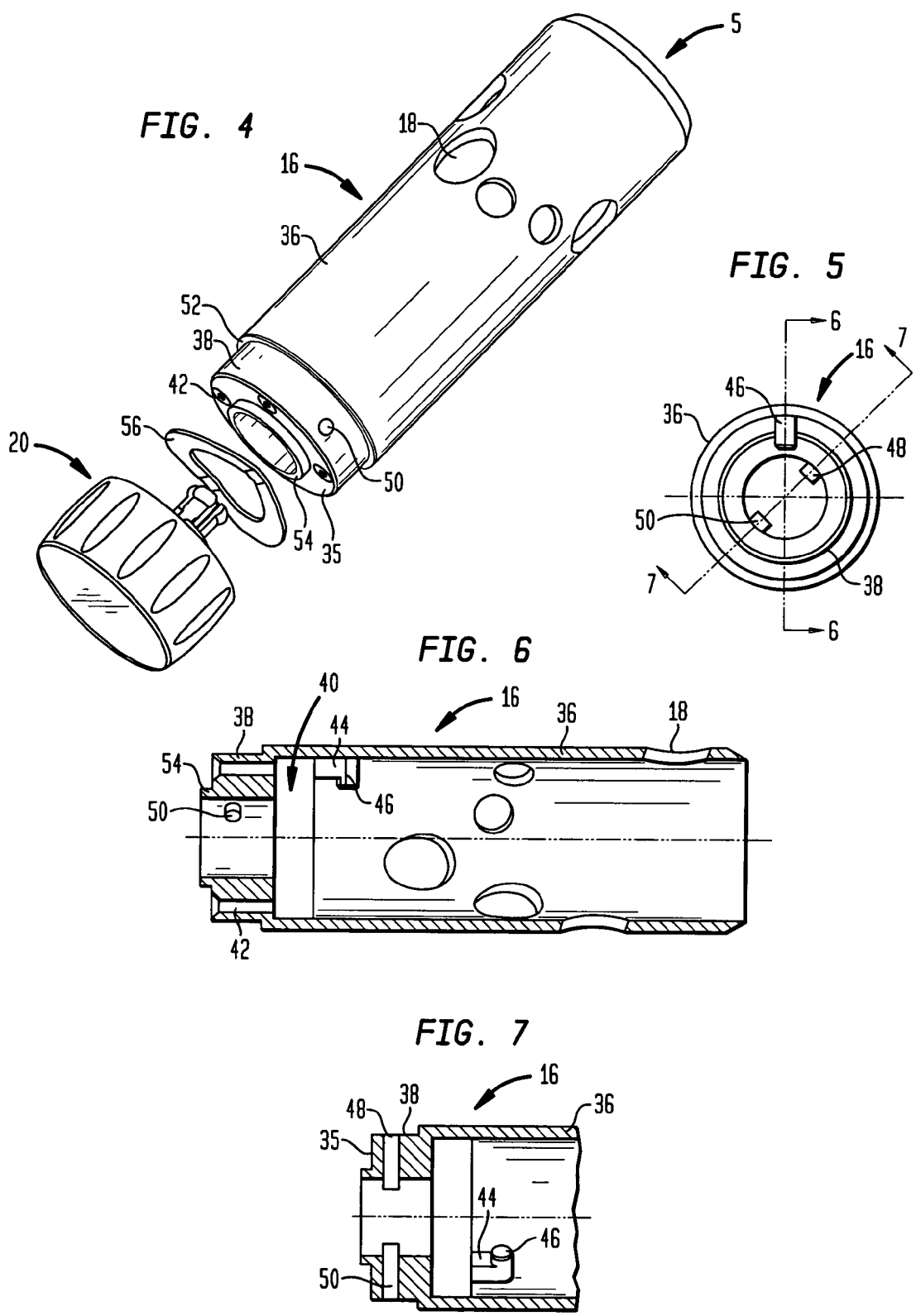

TARGETING DEVICE FOR LOCKING NAILS

BACKGROUND OF THE INVENTION

The invention relates to an aiming or targeting apparatus for locking nails. As is known, locking nails are bone nails which are provided with through cross-bores through which bone screws are passed. As is known the manufacture of bores in a bone for introducing bone screws through the nail cross-bores requires using an aiming or targeting apparatus. A typical targeting device or aiming apparatus is fixedly connected to the end of the bone nail to which the impaction force to drive in the nail is applied. This normally is the proximal end of the nail if it is introduced into the femur. The nail attachment portion of the targeting apparatus is connected to a targeting arm via a portion which mostly is of a U or L-shaped form. The targeting arm has provided therein cross-bores which are oriented with the bores in the locking nail when the nail is connected to the fixing portion of the targeting device in the way described herein. As was mentioned, since the locking nail has a plurality of cross-bores, which also include an oblique through bore for receiving a femoral neck screw, the individual cross-bores are located at different angles. Preferably, the bores in the targeting arm are of a similar shape. Targeting devices are shown in U.S. Pat. Nos. 5,176,681, 5,334,192 and 6,039,739. The teachings of U.S. Pat. No. 5,334,192 are incorporated herein by reference.

When a bore is made in a bone there naturally is only a need for the single associated bore in the targeting arm. A targeting and drilling sleeve-like guide is then passed through the bore in the arm and is advanced up to the bone and is used as an aid through which the first puncture is then made into the bone, after which drilling is done. To prevent the user from unintentionally choosing a wrong bore in the arm it is further known to push a sleeve over the targeting arm. The sleeve contains a cross-bore or pair of cross-holes which is/are oriented to align with a cross-bore in the targeting arm when the sleeve is slid onto the arm. For example, if four different through bores are provided in the targeting arm four sleeves per targeting apparatus are required to be provided. Since a series of targeting arm sleeves are required for a locking nail each associated sleeve needs to be selected and slid onto the targeting arm. The provision of multiple sleeves requires an expenditure which is not insignificant.

SUMMARY OF THE INVENTION

It is the object of the invention to provide a targeting apparatus in which both manufacturing costs and operative costs are reduced. Such a targeting device for guiding a drill into cross-bores of a bone nail implanted in a long bone has an attachment element for attaching the targeting device to the bone nail. A guide arm is coupled to the attachment element. The guide arm has a portion extending along an axis generally parallel to a longitudinal axis of the long bone and of the nail. The arm includes at least two bores alignable with the nail cross-bores. A sleeve is rotatably mounted on the targeting arm for rotation about the arm longitudinal axis. The sleeve has a plurality of apertures axially spaced thereon with respect to said longitudinal axis with each aperture alignable with one of the at least two bores on said guide arm.

As stated, the targeting arm has supported thereon a rotatable sleeve which while being rotatable, is substantially axially displaceable and has a series of cross-bores which are circumferentially and axially spaced wherein, in predetermined rotational positions of the rotatable sleeve, only a single aperture or pair of apertures of a plurality of apertures is aligned with a bore of the targeting arm. Thus, in the inventive targeting apparatus, only one sleeve is required to be disposed on the targeting arm and will permanently remain on the targeting arm. One pair of cross-apertures each may be oriented to one cross-bore in the targeting arm, depending on its rotational position. Appropriate markings may be provided on the targeting arm or targeting sleeve and will cause the user to easily realize at which rotational position of the rotatable sleeve a cross-bore of the targeting arm is to be used. Since the rotatable sleeve may involuntarily undergo rotation unless specific provisions are made, it is further advantageous if the inventive targeting apparatus includes a detent which catchingly locks the rotatable sleeve on the targeting arm in an occupied rotational position.

As was described, in a rotational position selected, a targeting and drilling guide sleeve is advanced through the apertures of the rotatable sleeve and through the cross-bore of the targeting arm until it bears on the bone. Unless provisions are made the targeting and drilling sleeve can shift unintentionally. To avoid this, an aspect of the invention provides that the targeting arm has connected thereto a tightening device which produces a slight axial displacement of the rotatable targeting arm sleeve of the opening of the rotatable sleeve on the targeting arm. Only a minimal axial displacement of the rotatable sleeve will be sufficient to firmly clip and clamp the targeting and drilling sleeve in position. This axial displacement is possible because of the tolerance which exists within the fixed axial location of the displaceable sleeve.

To allow the sleeve to be axially supported on the targeting arm in an approximately non-displaceable way, an aspect of the invention provides that the sleeve, at the rear or distal end, has an internal radial projection which cooperates with an annular groove of the targeting arm. This projection may also be used to cooperate with detent recesses of the targeting arm to engage them on the targeting arm in the predetermined rotational positions of the rotatable sleeve.

Various constructional options are imaginable to slightly displace the rotatable sleeve for the purpose of clamping the targeting and drilling sleeve. One way provides that the tightening device has a rotary knob which, located at the free or distal end of the rotatable sleeve, is rotatably mounted by means of a central trunnion in a recess of the targeting arm, but cannot be displaced axially. The pressure-exerting knob and the rotatable sleeve cooperate via a guide cam and a cam follower so that, upon rotation of the rotary knob, the rotatable sleeve is biased in an axial direction. For this purpose, the rotary knob may be of a hollow cylindrical configuration and, centrally at the inside at the bottom, have an axial lug at the upper end of which a trunnion is disposed which cooperates with a recess of the targeting arm. The circumference of the lug has disposed thereon an annular groove which cooperates with at least one radial protrusion of the rotatable sleeve. The annular groove portion is connected to the proximal or free end of the lug via an axially parallel groove for the purpose of introducing the radial protrusion into the annular groove. The annular groove is inclined to some extent so that if the annular groove is rotated the rotatable sleeve will be biased in an axial direction.

Another aspect of the invention provides that a spring which biases the components against each other is disposed between the pressure-exerting knob and the free end of the rotatable sleeve.

BRIEF DESCRIPTION OF THE DRAWINGS

An embodiment of the invention will be described in more detail below with reference to the drawings.

FIG. 2 shows a side view of the targeting apparatus of FIG. 1 without the rotatable sleeve;

FIG. 3 shows a section through the representation of FIG. 2 along line 3—3;

FIG. 4 shows a perspective view of the rotatable sleeve of the targeting apparatus of FIG. 1 including a rotatable sleeve;

FIG. 5 shows an end view of the rotatable sleeve of FIG. 4 in the direction of arrow 5;

FIG. 6 shows a section through the rotatable sleeve of FIG. 5 along line 6—6;

FIG. 7 shows a section through the rotatable sleeve of FIG. 5 along line 7—7 which illustrates only or some part of the sleeve length;

DETAILED DESCRIPTION

Figure 1:
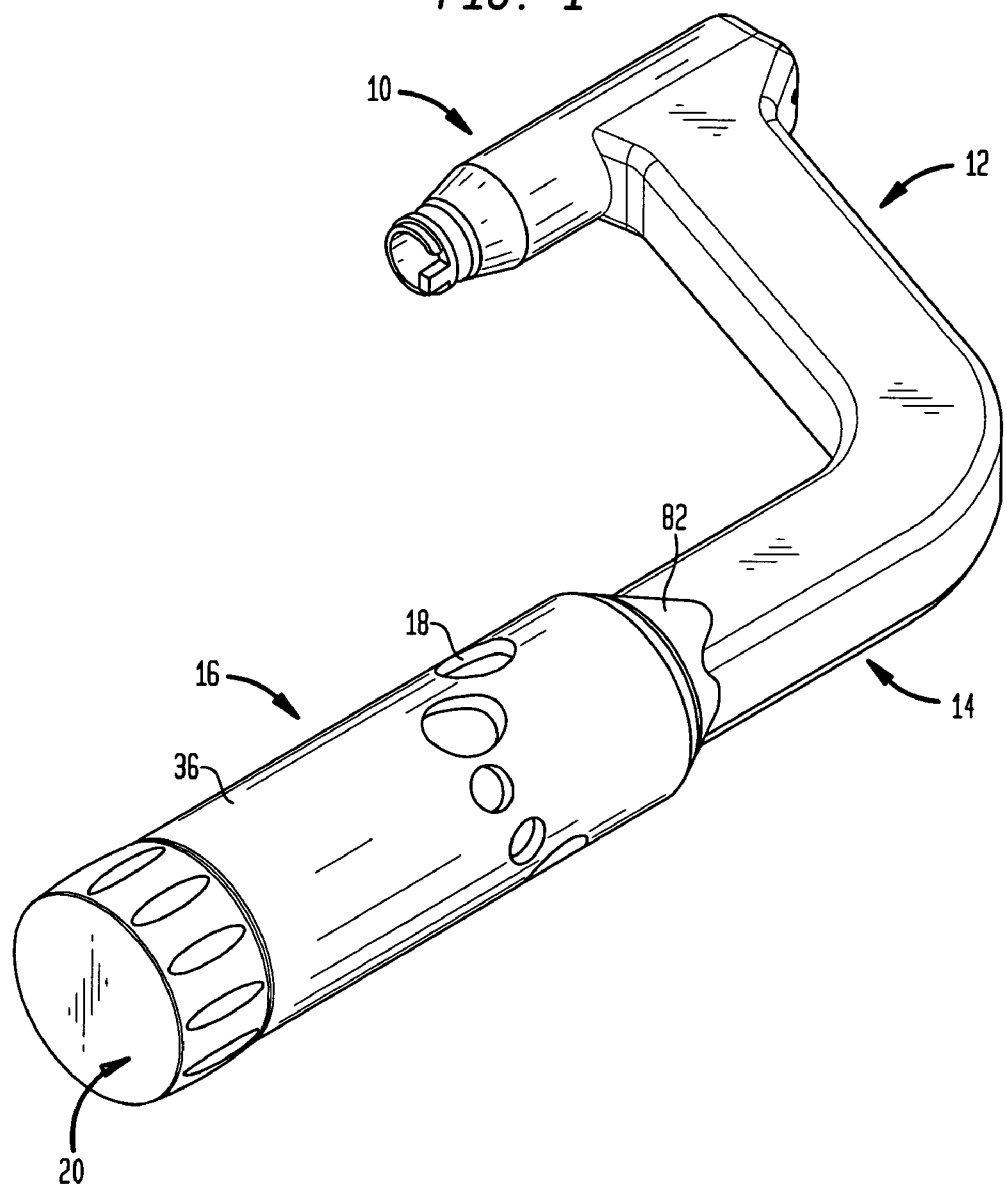
FIG. 1 shows a perspective view of a targeting apparatus of the invention.

Referring to FIG. 1, there is shown the targeting apparatus of the present invention which has a mounting portion 10 which is meant to be appropriately connected to an end of a locking nail which is not shown. This mounting method is well known and will not be discussed since it forms part of the state of the art.

Via a generally U or L-shaped connecting portion 12, the mounting portion 10 has fixedly connected thereto a targeting arm 14. The targeting arm 14 rotatably supports a rotatable sleeve 16 about its distal end. Around its circumference, the rotatable sleeve 16 has a plurality of cross-apertures 18 which are disposed axially at different locations and are formed at different angles. The purpose of these apertures will be discussed hereinbelow. A rotary knob 20 is arranged at the free end of the targeting sleeve 16.

Mounting portion 10, connecting portion 12, and targeting arm 14 are shown in greater detail in FIGS. 2 and 3. As can be seen targeting arm 14, in the lower distal region, has an approximately cylindrical portion 22 which is provided with a series of cross-bores 24. In the preferred embodiment, a total of 4 cross-bores are provided all of which are arranged at different angles of which one bore corresponds to a dual bore. The axes of cross-bores 24 are oriented with respect to the axes of holes or cross-bores of a locking nail (not shown) once it is firmly connected to the mounting portion 10.

Adjacent its free or outer end 25, targeting arm 14 has an annular groove 26 which is connected to free end 25 of targeting arm 14 via an axially parallel groove 28. At the center of free end 25, a recess or bore 30 is formed which has an inner annular groove 32 which forms an undercut in bore 30. As can be seen from FIG. 2, circumferentially spaced detent recesses 34 are provided, the function of which will be explained below. Recesses 34 are formed adjacent to the wall surface of annular groove 26.

The structure of the rotatable sleeve 16 can be seen from FIGS. 4 to 7. In the preferred embodiment, the sleeve has a cylindrical portion 36 with the inside diameter of portion 36 which largely extends over the full length of the rotatable sleeve 16, is slightly larger than that of the cylindrical portion 22 of targeting arm 14. On the left of FIGS. 4, 6 and 7, an extension portion 38 and has an inner diameter which is smaller than the inner diameter of portion 36. A blocking ring 40 is positioned against the step thus formed and is attached to sleeve 16 by fixing screws which are screwed in through axially parallel bores 42. The blocking ring 40 has a lug 44 and a projection 46, which faces radially inwardly from axially parallel lug 44. As shown in FIGS. 6 and 7, in the preferred embodiment, two radial pins 48, 50 extend into the interior of portion 38 to some extent. In the preferred embodiment, pins 48, 50 are diametrically disposed in the portion 38 and are press fit therein.

It further can be seen that the outside diameter of the portion 38 is slightly smaller than is the outside diameter of the portion 36 so as to define an appropriate shoulder 52. Finally, at its free end 35, the portion 38 has disposed thereon an axially extending collar 54 which serves for accommodating a curved washer 56 which is placed on collar 54 and bears against the front portion 35 of rotatable sleeve 16.

Figure 8:
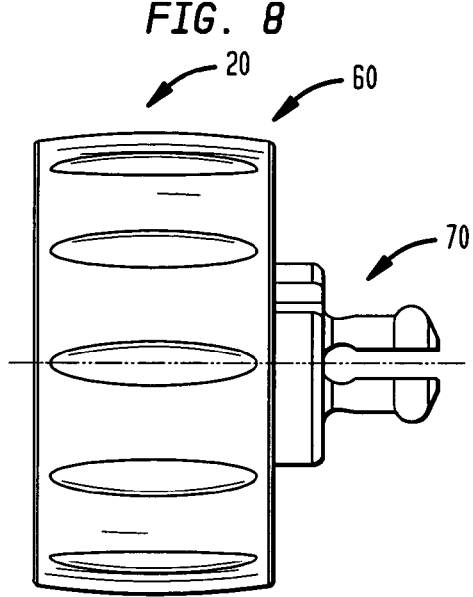
FIG. 8 shows the rotary knob of FIG. 4 in a side view.
Figure 9:
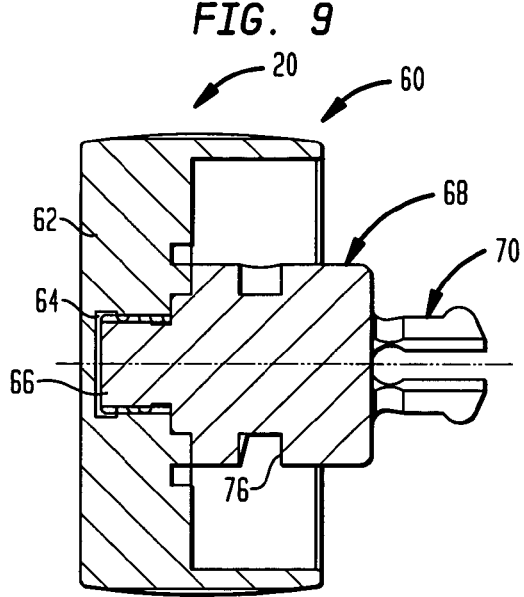
FIG. 9 shows a section through the rotary knob of FIG. 8.
Figure 10:
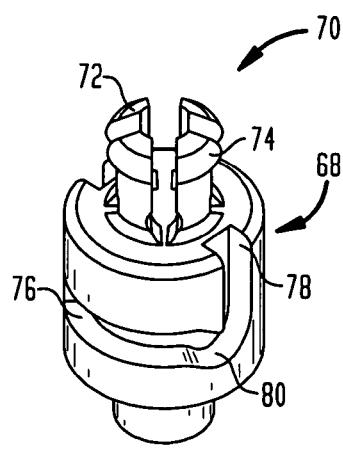
FIG. 10 shows a perspective view of the lug which engages of the rotatable sleeve and knob of FIGS. 8 and 9.

The structure of rotary knob 20 can be seen from FIGS. 8 to 10. Knob 20 has a partially hollow cylindrically shaped part 60 the bottom of which has a recess 64 for receiving a lug or adaptor 68. Recess 64 has inserted therein an axial projection 66 of axial lug 68 which is fixed therein either by gluing or by a threaded joint. At the right-hand end, the lug has a trunnion 70 which is shaped as a clip with four arms 72 which are disposed to be circumferentially spaced and to have gap therebetween and have a radial enlargement 74 at the outer end.

In the preferred embodiment, as shown in FIG. 10, lug 68 further has two diametrically opposed annular groove portions 76 which are connected to the upper end of the lug 68 via an axially parallel groove portion 78 where it meets groove 76. An indentation 80 is provided at the inner end of the axially parallel groove portion 78. The annular groove portion 76 is provided with a small descent or downward slope which starts from the indentation 80 in moving to the left of FIG. 10. It is understood that this feature also applies to the annular groove portion 76 on the opposed side of lug 68.

For assembly, the rotatable sleeve 16 is slid onto the cylindrical portion 22 of targeting arm 14, the radial projection 46 being adapted to engage the annular groove 26 via the axially parallel groove 28 if the sleeve is slightly rotated. The detent recesses 34 allows one to fix the rotational position of the rotatable sleeve 16 in predetermined rotational positions such that at least one aperture 18 and preferably two apertures on opposite sides of the rotatable sleeve 16 are oriented to a bore 24 of targeting arm 14.

The trunnion 70 of the lug 68 is introduced into the recess 30 through the curved washer 56 and the collar 54 with the enlargements 74 of the trunnion 70 being captured in the annular groove 32. This axially secures the rotary knob which, however, can be rotated. While the trunnion 70 is introduced in the way described the lug 68, which is illustrated at a larger scale in FIGS. 8 to 10, engages the interior of the portion 38 of the sleeve 16. At this stage, the rotary knob 20 is required to be arranged in its rotational position so as to orient the axially parallel grooves 78 to the pins 48, 50. As soon as the indentation 80 is reached the rotary knob 20 is slightly rotated in a clockwise sense until the pins 48, 50 enter the annular groove portion 76. If the rotary knob 20 continues to be rotated the rotatable sleeve 76 is pulled towards the rotary knob, as a result. If the targeting and drilling sleeve, which is not shown, is in a cross-bore 24 and a respective aperture 18 this sleeve will be clamped when the rotatable sleeve is displaced as described.

In the arrangement described, the cylindrical recessed part of the rotary knob is on the portion 38 of the sleeve 16 as shown from FIG. 1. This also makes it evident that the outer circumference of the knurled rotary knob 20 has approximately the same diameter as has the outer diameter of portion 36 of the rotatable sleeve 16. An appropriately gentle transition region 82 is formed between the arm portion with rotatable sleeve 16 and the adjoining portion of targeting arm 14, which preferably is of a rectangular shape in cross-section. While a pair of axially spaced apertures located on opposite sides of sleeve 16 are preferred for each angled bore 24, it is of course possible to design a sleeve 16 having apertures on one side only and having, for example, an enlarged window located at 180° around the sleeve 16 from the aperture 18.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A targeting apparatus for locking nails, comprising:
a first portion which is adapted to be fixedly connected to an end of a locking nail, a targeting arm which is connected to the first portion via a connecting portion, the targeting arm having a plurality of bores for guiding a drill wherein the bores are disposed at different angles; and
a rotatable sleeve mounted on said arm and having a series of apertures which are circumferentially and axially spaced such that at a selected rotational position of the rotatable sleeve, at least one aperture is aligned with a bore of the targeting arm and detent means are provided to lock the rotatable sleeve on the targeting arm in the selected rotational position.

2. The targeting apparatus as set forth in claim 1 further comprising a drill sleeve extending through at least one aperture on said sleeve and one bore of said targeting arm wherein the targeting arm has connected thereto a tightening device which produces a slight axial displacement of the rotatable sleeve on the targeting arm to clamp the drill sleeve.

3. The targeting apparatus as set forth in claim 2 wherein the sleeve has a first end having an internal projection which cooperates with an annular groove formed adjacent an outer end of the targeting arm.

4. The targeting apparatus as set forth in claim 3 wherein the projection additionally cooperates with detent recesses of the targeting arm which face the annular groove.

5. The targeting apparatus as set forth in claim 2 wherein the tightening device has a rotary knob with a trunnion, the knob rotatably mounted on an outer end of the rotatable sleeve, said trunnion engaging a recess in the outer end of the targeting arm, the rotatable knob and rotatable sleeve engaging via a guide cam surface and a cam follower so that, upon rotation of the knob, the rotatable sleeve is moved in an axial direction to clamp said drill sleeve.

6. The targeting apparatus as set forth in claim 5, wherein the rotatable knob has a centrally located adaptor having a trunnion for engaging said targeting arm, the trunnion having a circumferential annular groove portion forming the cam surface which cooperates with a radial protrusion forming the cam follower of the rotatable sleeve, the adaptor having a free end and said circumferential annular groove portion connected to the adaptor free end via an axially oriented groove which engages the protrusion and introduces the protrusion into the annular groove portion.

7. The targeting apparatus as set forth in claim 6 wherein the adaptor is removably mounted in the rotary knob.

8. The targeting apparatus as set forth in claim 7 wherein a spring is disposed between the sleeve and the knob which spring biases the components against each other.

9. The targeting apparatus as set forth in claim 8 wherein the spring is a curved washer.

10. A targeting device for guiding a drill into cross-bores of a bone nail implanted in a long bone, comprising:
a means for attaching the targeting device to the bone nail;
a guide arm coupled to said means for attaching the targeting device, said guide arm having a portion extending along a central axis generally parallel to a longitudinal axis of the long bone, said arm including at least two bores alignable with the nail cross-bores; and
a sleeve rotatably mounted on said arm for rotation about said central axis, said sleeve having at least two apertures axially spaced thereon said guide with respect to said longitudinal axis, one of said at least two apertures alignable with one of said at least two bores on said guide arm.

11. The targeting device as set forth in claim 10 further comprising a drill guide insertable through said aligned apertures in both said guide arm and said sleeve.

12. The targeting device as set forth in claim 11 further comprising means for locking said sleeve in a selected rotational position on said guide arm.

13. The targeting device as set forth in claim 12 further comprising means for axially moving said sleeve on said guide arm to clamp said drill guide in said aligned apertures on said guide arm and said sleeve.

14. The targeting device as set forth in claim 11 further comprising a knob rotatably coupled to both said guide arm and said sleeve.

15. The targeting arm as set forth in claim 14 wherein a cam and a cam follower are respectively mounted on one of said knob and said sleeve such that relative rotational movement between said knob and said sleeve causes relative axial movement between said guide arm and said sleeve with respect to said central axis to clamp said drill guide in said aligned apertures of said guide arm and said sleeve.

16. The targeting arm as set forth in claim 15 further comprising a spring biasing said sleeve axially away from said knob to release said cam and cam follower engagement.

17. The targeting arm as set forth in claim 16 wherein said cam is a groove on said knob and said cam follower is a pin mounted on said sleeve for engagement with said groove.

18. The targeting arm as set forth in claim 10 wherein said sleeve includes a pair of apertures spaced from each other at 180° around an outer circumference of said sleeve, each aperture of said pair alignable with one of said at least two bores on said guide arm.

19. A targeting device for guiding a drill into cross-bores of a bone nail implanted in a long bone, comprising:
a coupling for attaching the targeting device to the bone nail;
a guide arm coupled to said coupling for attaching the targeting device, said guide arm having an aiming portion extending along a central axis generally parallel to a longitudinal axis of the long bone, said arm including at least two bores alignable with the nail cross-bores;

a sleeve rotatably mounted on said arm for rotation about said central axis, said sleeve having a plurality of apertures axially spaced on said guide with respect to said central axis each alignable with a different one of said at least two bores on said guide arm; and a knob rotatably mounted on said sleeve, wherein a cam and a cam follower are respectively mounted on one of said knob and said sleeve such that relative rotational movement between said knob and said sleeve causes relative axial movement between said guide arm and said sleeve with respect to said central axis to clamp said drill guide in said aligned apertures of said guide arm and said sleeve.

* * * * *

UNITED STATES PATENT AND TRADEMARK OFFICE
CERTIFICATE OF CORRECTION

PATENT NO. : 7,077,847 B2
APPLICATION NO. : 10/389542
DATED : July 18, 2006
INVENTOR(S) : Peter Pusnik and Sabine Bigdeli-issazadeh It is certified that error appears in the above-identified patent and that said Letters Patent is hereby corrected as shown below:

Column 6, line 25, cancel "said guide".

Signed and Sealed this

Thirtieth Day of January, 2007

JON W. DUDAS
*Director of the United States Patent and Trademark Office*